US012630487B2

(12) United States Patent
Miyake et al.

(10) Patent No.: US 12,630,487 B2
(45) Date of Patent: May 19, 2026

(54) METHOD FOR INTRODUCING DEUTERATED LOWER ALKYL INTO AMINE MOIETY OF COMPOUND CONTAINING SECONDARY AMINE

(71) Applicant: OTSUKA PHARMACEUTICAL CO., LTD., Tokyo (JP)

(72) Inventors: Masahiro Miyake, Osaka (JP); Masashi Hayashi, Osaka (JP); Yuya Nakai, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 1039 days.

(21) Appl. No.: 17/429,054

(22) PCT Filed: Mar. 12, 2020

(86) PCT No.: PCT/JP2020/010873
§ 371 (c)(1),
(2) Date: Aug. 6, 2021

(87) PCT Pub. No.: WO2020/184670
PCT Pub. Date: Sep. 17, 2020

(65) Prior Publication Data
US 2022/0127206 A1     Apr. 28, 2022

(30) Foreign Application Priority Data

Mar. 13, 2019     (JP) ................................. 2019-045857

(51) Int. Cl.
| | |
|---|---|
| C07B 59/00 | (2006.01) |
| C07C 253/30 | (2006.01) |
| C07D 207/09 | (2006.01) |
| C07D 209/34 | (2006.01) |
| C07D 213/75 | (2006.01) |
| C07D 215/58 | (2006.01) |
| C07D 221/04 | (2006.01) |
| C07D 295/023 | (2006.01) |
| C07D 401/04 | (2006.01) |
| C07D 401/12 | (2006.01) |
| C07D 401/14 | (2006.01) |
| C07D 403/04 | (2006.01) |
| C07D 403/06 | (2006.01) |
| C07D 417/04 | (2006.01) |
| C07D 451/10 | (2006.01) |
| C07D 471/14 | (2006.01) |
| C07D 487/04 | (2006.01) |
| C07D 495/04 | (2006.01) |
| C07D 498/06 | (2006.01) |
| C07D 513/14 | (2006.01) |
| C07F 9/6558 | (2006.01) |

(52) U.S. Cl.
CPC .......... *C07B 59/001* (2013.01); *C07C 253/30* (2013.01); *C07D 207/09* (2013.01); *C07D 209/34* (2013.01); *C07D 213/75* (2013.01);
*C07D 215/58* (2013.01); *C07D 221/04* (2013.01); *C07D 295/023* (2013.01); *C07D 401/04* (2013.01); *C07D 401/12* (2013.01); *C07D 401/14* (2013.01); *C07D 403/04* (2013.01); *C07D 403/06* (2013.01); *C07D 417/04* (2013.01); *C07D 451/10* (2013.01); *C07D 471/14* (2013.01); *C07D 487/04* (2013.01); *C07D 495/04* (2013.01); *C07D 498/06* (2013.01); *C07D 513/14* (2013.01); *C07F 9/65583* (2013.01); *C07B 2200/05* (2013.01)

(58) Field of Classification Search
None
See application file for complete search history.

(56) References Cited

U.S. PATENT DOCUMENTS

| | | | |
|---|---|---|---|
| 2008/0280936 | A1 | 11/2008 | Tung |
| 2018/0346498 | A1 | 12/2018 | Zhang et al. |
| 2019/0183885 | A1 | 6/2019 | Vepachedu et al. |
| 2020/0407326 | A1 | 12/2020 | Nakai et al. |

FOREIGN PATENT DOCUMENTS

| | | |
|---|---|---|
| CN | 108675959 A | 10/2018 |
| CN | 110028433 A | 7/2019 |
| JP | 2014-520140 A | 8/2014 |
| JP | 2018-536667 A | 12/2018 |
| WO | 9911641 | 3/1999 |
| WO | 2008/137474 A1 | 11/2008 |
| WO | 2012/176066 A1 | 12/2012 |
| WO | 2017/088784 A1 | 6/2017 |
| WO | 2018/039642 A1 | 3/2018 |
| WO | 2019/049918 A1 | 3/2019 |

OTHER PUBLICATIONS

Hedvig Bölcskei et al., "Synthesis of deuterated dextromethorphan derivatives", ARKIVOC, vol. 3, Jan. 1, 2008 (Jan. 1, 2008), pp. 182-193 (12 pages total).
Ian Fellows et al, "Simple methods for the labelling of N-methyl amines using isotopically labelled methyl iodide", Journal of Labelled Compounds and Radiopharmaceuticals, John Wiley, GB, vol. 41, No. 12, Jan. 1, 1998 (Jan. 1, 1998), pp. 1127-1143 (17 pages total).
Heinkele G et al, "Synthesis of [$^2$H$_3$]-dextromethorphan and its major urinary metabolites [$^2$H$_3$]-dextrorphan and [$^2$H$_3$]-dextrorphan-β-glucoronide", Journal of Labelled Compounds and Radiopharmaceuticals, John Wiley, GB, vol. 45, Jan. 1, 2002 (Jan. 1, 2002), pp. 1153-1158 (6 pages total).
International Search Report dated Apr. 21, 2020 from the International Searching Authority in International Application No. PCT/JP2020/010873.

(Continued)

*Primary Examiner* — Po-Chih Chen
(74) *Attorney, Agent, or Firm* — Sughrue Mion, PLLC

(57) ABSTRACT

The present invention relates to a method of mono-deuterated-lower-alkylating the amine part in a compound having an amine protected with an aralkyl, which comprises introducing mono-deuterated lower-alkyl into the amine with a deuterated-lower-alkylating agent under neutral or basic condition, and then deprotecting the aralkyl group.

9 Claims, No Drawings

(56)                    References Cited

OTHER PUBLICATIONS

International Preliminary Report on Patentability with the translation of Written Opinion dated Sep. 23, 2021 from the International Bureau in International Application No. PCT/JP2020/010873.
International Search Report dated Nov. 7, 2018 from the International Searching Authority in International Application No. PCT/JP2018/032983, corresponding to U.S. Appl. No. 16/644,084.
International Preliminary Report on Patentability with the translation of Written Opinion dated Mar. 10, 2020 from the International Bureau in International Application No. PCT/JP2018/032983, corresponding to U.S. Appl. No. 16/644,084.
Extended European Search Report dated Dec. 2, 2022 in European Application No. 20770660.7.
Canadian Office Action Issued Mar. 10, 2025 in Application No. 3132953.

METHOD FOR INTRODUCING DEUTERATED LOWER ALKYL INTO AMINE MOIETY OF COMPOUND CONTAINING SECONDARY AMINE

CROSS REFERENCE TO RELATED APPLICATIONS

This application is a National Stage of International Application No. PCT/JP2020/010873 filed Mar. 12, 2020, claiming priority based on Japanese Patent Application No. 2019-045857 filed Mar. 13, 2019.

TECHNICAL FIELD

The present invention relates to a method of introducing deuterated lower-alkyl into a secondary amino group in a compound having the secondary amine, in more detail, a method of deuterated-lower-alkylating a linear or chained amine group whose amino nitrogen is already protected with an aralkyl, under neutral or basic condition.

BACKGROUND ART

Drug substances are generally metabolized with an enzyme in liver and thereby the effect, thereof disappears. Thus, the improvement of the metabolism is expected to bring in some therapeutic advantages such as safety, availability, tolerability, and utility.

The structure of the metabolic site, which is variable with metabolism-type, may depend on the whole chemical structure of drug substances, and N-methyl is one of the main metabolic sites. It has been known that a drug substance having N-methyl therein can get inactivated about its effect when the N-methyl is demethylated. Thus, if hydrogen atom(s) in N-methyl is replaced by deuterium atom(s), the character of the methyl site can be changed, which is expected to bring in delaying the N-demethylation to improve the metabolic stability, further which is expected to bring in the therapeutic advantages mentioned above. Hence, many trials have been done until now (Patent Literature 1, Non-Patent Literatures 1 and 2).

A method of replacing hydrogen atom by deuterium atom is disclosed, in which deuterated methyl is incorporated into a piperazine derivative by reacting with methyl-$d_3$ 4-methylbenzenesulfonate (Patent Literature 2). The incorporation method produces N,N-dimethyl form as a by-product. However, it is hard to prevent the N,N-dimethylation, and the method has a problem of reducing the yield.

PRIOR ART

Patent Reference

[Patent Literature 1] WO 2008/137474
[Patent Literature 2] WO 2017/088784

Non-Patent Reference

[Non-patent Literature 1] ARKIVOC, (iii) 182-193 (2008)
[Non-patent Literature 2] J Label Compd Radiopharm, 45, 1153 (2002)

SUMMARY OF INVENTION

Technical Problem

It has been desired to develop a method of introducing mono-deuterated lower-alkyl into a linear or chained secondary amine while reducing the production of by-products, which has broad utility and brings in high yield.

Solution to Problem

The present, inventors have extensively studied and then have found that the desired N-mono-deuterated lower-alkyl compound can be prepared from a linear or chained secondary amine compound in high yield without producing its di-deuterated lower-alkylated by-product, by replacing the hydrogen atom in the secondary amine by aralkyl such as benzyl, deuterated-lower-alkylating the obtained amine derivative under neutral or basic condition, and then eliminating the aralkyl. Based upon the new findings, the present invention has been completed.

The present invention includes the following embodiments.

(Item 1) A method of introducing a mono-deuterated lower-alkyl into a secondary amine in a compound having the secondary amine, comprising
  replacing the hydrogen atom in the secondary amine by an aralkyl,
  lower-alkylating the obtained tertiary amine with a deuterated-lower-alkylating agent under neutral or basic condition, and then
  eliminating the aralkyl group.

(Item 2) The method of Item 1, wherein the secondary amine is not in a piperidine ring.

(Item 3) The method of Item 1 or 2, wherein the deuterated lower-alkyl is deuterated methyl or deuterated ethyl, and the deuterated-lower-alkylating agent is deuterated-methylating agent or deuterated-ethylating agent.

(Item 4) The method of any one of Items 1-3, wherein the deuterated lower-alkyl is deuterated methyl, and the deuterated-lower-alkylating agent is methyl-$d_3$ methanesulfonate, methyl-$d_3$ benzenesulfonate, methyl-$d_3$ 4-methylbenzenesulfonate, methyl-$d_3$ 2-nitrobenzenesulfonate, methyl-$d_3$ 4-nitrobenzenesulfonate, dimethyl-$d_6$ sulfate, dimethyl-$d_6$ carbonate, methyl-$d_3$ trifluoromethanesulfonate, bromomethyl-$d_3$, or iodomethyl-$d_3$.

(Item 5) The method of any one of Items 1-3, wherein the deuterated lower-alkyl is deuterated ethyl, and the deuterated-lower-alkylating agent is ethyl-$d_5$ methanesulfonate, ethyl-$d_5$ benzenesulfonate, ethyl-$d_5$ 4-methylbenzenesulfonate, ethyl-$d_5$ 2-nitrobenzenesulfonate, ethyl-$d_5$ 4-nitrobenzenesulfonate, diethyl-$d_{10}$ sulfate, diethyl-$d_{10}$ carbonate, ethyl-$d_5$ trifluoromethanesulfonate, bromoethyl-$d_5$, or iodoethyl-$d_5$.

(Item 6) The method of any one of Items 1-5, wherein the aralkyl is benzyl derivative.

(Item 7) The method of Item 6, wherein the benzyl derivative is benzyl or 4-methoxybenzyl.

(Item 8) The method of Item 6 or 7, wherein the elimination of the aralkyl group is carried out by hydrogenation.

(Item 9) The method of any one of Items 1-8, wherein the basic condition is adjusted with sodium carbonate, cesium carbonate, potassium carbonate, sodium bicarbonate, potassium bicarbonate, sodium hydride, potassium hydride, sodium hydroxide, potassium hydroxide, sodium tert-butoxide, potassium tert-butoxide, alkyllithium (e.g. n-butyl lithium, sec-butyl lithium, tert-butyl lithium, and n-hexyl lithium), lithium amide (e.g. lithium diisopropylamide, and lithium hexamethyldisilazide), sodium methoxide, or tert-amine (e.g. trimeth-ylamine, triethylamine, triisopropylamine, and diiso-propylethylamine).

(Item 10) The method of any one of Items 1-9, wherein the compound having a secondary amine is selected from the group consisting of piperazine derivative, pyrrolidine derivative, azepane derivative, diazepane derivative, and a chained amine compound.

Effect of the Invention

As for the method of incorporating deuterated lower-alkyl, into a secondary amine, the present invention makes it possible to effectively mono-deuterated-lower-alkylate the amine without producing its di-deuterated lower-alkylated by-product, by replacing the hydrogen atom in the amine by aralkyl temporarily, deuterated-lower-alkylating the obtained amine with a deuterated-lower-alkylating agent, and then deprotecting the aralkyl.

The present invention can suppress the production of a by-product such as N,N-di-deuterated lower-alkyl com-pound, thus the yield of the desired product based on an expensive $d_3$-methylating agent or $d_5$-ethylating agent can be maximized and additionally the residual unreacted amine compound can be minimized, and thereby the industrial manufacture cost can be reduced. Methyl-$d_3$ methane-sulfonate and methyl-$d_3$ benzenesulfonate which can be used as a $d_3$-methylating agent in the present invention can be prepared from highly pure deuterated methanol (CD$_3$OD, methanol-$d_4$) which is widely used as deuterium source, thus it is expected to bring in further costcut. In addition, deu-terated methanol which is a starting material of the deuter-ated-methylating agent having sulfonate group is highly safe in handling such as carriage since deuterated methanol has no mutagenesis like CD$_3$I.

DESCRIPTION OF EMBODIMENTS

Each phrase and term used herein are explained below.

The term "aralkyl" used herein for protecting a secondary amine denotes an alkyl group wherein one of hydrogen atoms in the alkyl is replaced by an aryl group, which includes, for example, benzyl derivative, in more detail, benzyl, 4-nitrobenzyl, 4-methoxybenzyl, 2-nitrobenzyl, 4-chlorobenzyl, 2,6-dichlorobenzyl, 4-methylbenzyl, and 2,4,6-trimethylbenzyl. Preferably, it is benzyl or 4-methoxy-benzyl.

Exemplified methods to introduce such aralkyl into a secondary amine include methods disclosed in T. W. Greene and P. G. M. Wuts, "Greene's Protective Groups in Organic Synthesis", 4th edition, Wiley, New York 2006, or similar methods. For example, they include a method of treating with a halogenated benzyl in the presence of a base, and a reductive amination in which an amine compound is reacted with a benzaldehyde compound to give its imine compound which is reduced with a reducing agent such as sodium borohydride, cyanosodium borohydride, and sodium triac-etoxyborohydride.

The elimination (deprotection) of an aralkyl may be also carried out according to methods disclosed in T. W. Greene and P. G. M. Wuts, "Greene's Protective Groups in Organic Synthesis", 4th edition, Wiley, New York 2006, or similar methods. For example, for benzyl or p-methoxybenzyl, the protecting group can be removed by hydrogenation with palladium catalyst, or under a mild acidic condition with DDQ, CAN, or the like.

The term "deuterated lower-alkyl" used herein denotes an alkyl in which one or more hydrogen atoms in the lower-alkyl is replaced by deuterium, wherein the lower-alkyl includes, for example, methyl and ethyl, and preferably methyl. And, regarding methyl or ethyl, it is preferably a deuterated lower-alkyl wherein all hydrogen atoms in the alkyl group are replaced by deuterium, which includes, for example, methyl-$d_3$ and ethyl-$d_5$. In the present invention, deuterium may be denoted by d, D, or $^2$H, and methyl group wherein all the three hydrogen atoms are replaced by deuterium atoms may be denoted by methyl-$d_3$, $d_3$-methyl, deuterated methyl, CD$_3$, [$^2$H$_3$]methyl, etc.

The "deuterated-lower-alkylating agent" has a structure that deuterated lower-alkyl is combined with a suitable leaving group, wherein the deuterated lower-alkyl includes the above-mentioned ones; and the leaving group Includes preferably halogen (such as iodine and bromine), sulfonate (such as methanesulfonate, benzenesulfonate, 4-methylben-zenesulfonate, 2-nitrobenzenesulfonate, 4-nitrobenzene-sulfonate, and trifluoromethanesulfonate), as well as sulfate and carbonate which are bivalent leaving groups bindable to two alkyl groups. The deuterated-lower-alkylating agent includes, for example, methyl-$d_3$ methanesulfonate, methyl-$d_3$ benzenesulfonate, methyl-$d_3$ 4-methylbenzenesulfonate, methyl-$d_3$ 2-nitrobenzenesulfonate, methyl-$d_3$ 4-nitrobenze-nesulfonate, dimethyl-$d_6$ sulfate, dimethyl-$d_6$ carbonate, methyl-$d_3$ trifluoromethanesulfonate, bromomethyl-$d_3$, iodomethyl-$d_3$, ethyl-$d_5$ methanesulfonate, ethyl-$d_5$ benze-nesulfonate, ethyl-$d_5$ 4-methylbenzenesulfonate, ethyl-$d_5$ 2-nitrobenzenesulfonate, ethyl-$d_5$ 4-nitrobenzenesulfonate, diethyl-$d_{10}$ sulfate, diethyl-$d_{10}$ carbonate, ethyl-$d_5$ trifluo-romethanesulfonate, bromoethyl-$d_5$, and iodoethyl-$d_5$, and preferably methyl-$d_3$ methanesulfonate, methyl-$d_3$ benzene-sulfonate, methyl-$d_3$ 4-methylsulfonate, methyl-$d_3$ 2-ni-trobenzenesulfonate, methyl-$d_3$ 4-nitrobenzenesulfonate, ethyl-$d_5$ methanesulfonate, ethyl-$d_5$ benzenesulfonate, ethyl-$d_5$ 4-methylbenzenesulfonate, ethyl-$d_5$ 2-nitrobenzene-sulfonate, and ethyl-$d_5$ 4-nitrobenzenesulfonate.

Among the "deuterated-lower-alkylating agent", an alky-lating agent having sulfonate group can be prepared by a conventional method with, for example, deuterated metha-nol or deuterated ethanol. As shown in Reference examples below, for example, it can be prepared by reacting sulfonyl chloride reagent and deuterated methanol or deuterated ethanol under basic condition.

Methyl-$d_3$ methanesulfonate can be prepared according to the method described in US patent publication No. 2008/0194529 A; methyl-$d_3$ benzenesulfonate can be prepared according to the method described in Journal of Labelled Compounds and Radiopharmaceuticals, 25, 1267 (1988); methyl-$d_3$ 4-methylsulfonate can be prepared according to the method described in Journal of Organic Chemistry, 81, 7675 (2016); and methyl-$d_3$ 4-nitrobenzenesulfonate can be prepared according to the method described in Physical Organic Chemistry, 11, 1741 (1991).

The deuterated-lower-alkylation of a secondary amine can be accomplished by replacing the hydrogen atom on the amine group of the secondary amine compound by an aralkyl and then reacting the obtained amine derivative with a deuterated-lower-alkylating agent under neutral or basic condition in an inert solvent. The "neutral condition" used herein means a natural pH which is derived from a starting material, a reagent, a solvent, etc., especially a state of non-adjusted pH, or a pH which is adjusted to around neutrality with a reagent used in the basic condition men-tioned below. For example, the pH is around the range of 6-8, preferably 6.5-7.5. The "basic condition" used heroin means a basic condition adjusted with sodium carbonate, cesium carbonate, potassium carbonate, sodium bicarbonate, potassium bicarbonate, sodium hydride, potassium hydride, sodium hydroxide, potassium hydroxide, sodium tert-butoxide, potassium tert-butoxide, alkyllithium (e.g. n-butyl lithium, sec-butyl lithium, tert-butyl lithium, n-hexyl lithium), lithium amide (e.g. lithium diisopropylamide, lithium hexamethyldisilazide), sodium methoxide, or tert-amine (e.g. trimethylamine, triethylamine, triisopropylamine, diisopropylethylamine), preferably with sodium carbonate, cesium carbonate, potassium carbonate, sodium bicarbonate, or potassium bicarbonate, and particularly preferably sodium bicarbonate. These basic reagents may be used as a single or a combination thereof. The amount of the basic reagent is generally 1 mole to 10 moles, preferably 1 mole to 6 moles, per mole of the starting material.

The deuterated-lower-alkylation of the present invention may be done in an inert solvent, and said inert solvent can be suitably chosen depending on the reaction condition, which includes, for example, water; an ether solvent such as dioxane, tetrahydrofuran, diethyl ether, 1,2-dimethoxyethane, diethylene glycol dimethyl ether, and ethylene glycol dimethyl ether; an aromatic hydrocarbon solvent such as benzene, toluene, and xylene; a lower-alcohol solvent such as methanol, ethanol, and isopropanol; a ketone solvent such as acetone and methyl ethyl ketone; and a polar solvent such as N,N-dimethylformamide (DMF), N,N-dimethylacetamide (DMA), dimethyl sulfoxide (DMSO), hexamethylphosphoric triamide, and acetonitrile. These inert solvents may be used as a single or a combination thereof.

The reactions of the present invention may be also done under ordinary pressure or increased pressure, under an inert gas atmosphere such as nitrogen and argon. The above reactions are done usually at room temperature to at 200° C., preferably at room temperature to at 150° C., and are completed generally in about 1-30 hours.

The compound having a secondary amine of the present invention should not be limited as long as the compound has a secondary amine structure, which includes compounds having piperazine, pyrrolidine, azepane, diazepane, or morpholine structure. And, these structures may be a single ring system as well as a part of a bicyclic, tricyclic, or tetracyclic system. In addition, they may be also a chained amine. The drug compound having N-alkylpiperazine into which a deuterated lower-alkyl can be introduced includes, for example, imatinib, gilteritinib, netupitant, abemaciclib, blonanserin, vardenafil, masitinib, olanzapine, nintedanib, levofloxacin, sildenafil, bosutinib, brigatinib, and mirtazapine. The drug compound having N-alkylpyrrolidine includes, for example, atropine, tropisetron, eletriptan, nicotine, phenserine, udenafil, and amisulpride. The drug compound having N-alkylazepane includes, for example, azelastine. The drug compound having N-alkyl-1,4-diazepane includes, for example, emedastine and CX-5461. The drug compound having N-alkyl-chained amine includes, for example, verapamil.

The present invention also encompasses an intermediate in use for preparing a drug compound having N-alkylamine into which a deuterated lower-alkyl can be introduced. For example, an amine compound substituted with a deuterated lower-alkyl which is prepared in the present invention can be attached to another structure in various manners to prepare various drug compounds with a deuterated lower-alkyl. The chemical structure of secondary amine here which is a basic structure of intermediate includes azetidine, pyrrolidine, piperidine, azepane, azocane, azepanone, piperazine, piperazinone, morpholine, indoline, isoindoline, dihydrobenzimidazole, indazoline, dihydrotriazolopyridazine, dihydroquinoline, tetrahydroquinoline, decahydroquinoline, dihydroisoquinoline, tetrahydroisoquinoline, tetrahydronaphthyridine, hexahydronaphthyridine, dihydroquinoxaline, tetrahydroquinoxaline, dihydroquinazoline, tetrahydroquinazoline, benzazepine, tetrahydrobenzazepine, tetrahydropyridoindole, dihydrophenanthridine, diazaspiroheptane, and azaspiroundecane.

In the preparation process of the present invention, an aralkyl-substituted amine compound prepared in a conventional manner can be reacted with a deuterated-lower-alkylating agent to form its amine compound quaternized with the deuterated-lower-alkyl temporarily without isolating its product, and deprotected by cleaving the aralkyl to obtain the desired compound wherein the secondary amine is mono-substituted with a deuterated lower-alkyl.

A=aralkyl, R=methyl, phenyl, etc.

In the present invention, the starting materials, intermediates, and/or desired compounds may be their salt compounds thereof, and the present invention also encompasses processes including such salt compounds. The salt compounds can be in acid addition salt form, or sometimes in salt form with a base, depending on the type of substituents. Said acid includes, for example, an inorganic acid such as hydrochloric acid, hydrobromic acid, nitric acid, sulfuric acid, and phosphoric acid; and an organic acid such as methanesulfonic acid, p-toluenesulfonic acid, acetic acid, oxalic acid, citric acid, tartaric acid, maleic acid, fumaric acid, malic acid, and lactic acid. Said base includes, for example, an inorganic base such as sodium hydroxide, potassium hydroxide, calcium hydroxide, sodium carbonate, potassium carbonate, sodium bicarbonate, and potassium bicarbonate; and an organic base such as methylamine, diethylamine, trimethylamine, triethylamine, ethanolamine, diethanolamine, triethanolamine, ethylenediamine, tris(hydroxymethyl)methylamine, dicyclohexylamine, N,N-dibenzylethylenediamine, guanidine, pyridine, picoline, and choline; and additionally an ammonium salt. And, said salt may be a salt with an amino acid such as lysine, arginine, aspartate, and glutamate.

All disclosures in the patent literatures and non-patent literatures cited herein are entirely incorporated by reference herein.

EXAMPLES

The present invention is explained in more detail in the following by referring to Reference examples and Examples, however, the present invention should not be limited thereto, and the examples may be varied within the scope of the present invention.

In the present specification, the abbreviations shown below may be used.

| Abbreviation | Formal name |
|---|---|
| Bn | benzyl |
| AcOEt | ethyl acetate |
| AcOH | acetic acid |
| BBr$_3$ | boron tribromide |
| DCM | dichloromethane |
| DMF | N,N-dimethylformamide |
| Et$_2$O | diethyl ether |
| EtOH | ethanol |
| HCl | hydrochloric acid |
| IPA | 2-propanol |
| K$_2$CO$_3$ | potassium carbonate |
| KI | potassium iodide |
| MeCN | acetonitrile |
| MeOH | methanol |
| MTBE | methyl tert-butyl ether |
| NaHCO$_3$ | sodium bicarbonate |
| NaI | sodium iodide |
| NaOH | sodium hydroxide |
| NaOtBu | sodium t-butoxide |
| NH$_4$Cl | ammonium chloride |
| Pd/C | palladium-supported carbon |
| Pd(OH)$_2$/C | palladium hydroxide-supported carbon |
| TEA | triethylamine |
| THF | tetrahydrofuran |

$^1$H-NMR (proton nuclear magnetic resonance spectrum) was measured with Fourier transform NMR (Bruker AVANCE NEO (400 MHz) or Bruker AVANCE III HD (500 MHz).

Reference Examples 1-5

Preparation of (9S,13S,14S)-3-(methoxy-d$_3$)-17-(methyl-d$_3$)-morphinan

HBr

The desired compound was prepared with any one of deuterated-methylating agents shown in Table 1.

TABLE 1

| | Deuterated-methylating agent | Process | Yield | UPLC Purity |
|---|---|---|---|---|
| Reference example 1 | methyl-d$_3$ methanesulfonate | 1 | 98.2% | 87.1% |
| Reference example 2 | methyl-d$_3$ benzenesulfonate | 1 | 92.6% | >98% |
| Reference example 3 | methyl-d$_3$ 4-methylbenzenesulfonate | 1 | 98.9% | >99.8% |
| Reference example 4 | methyl-d$_3$ 4-nitrobenzenesulfonate | 1 | 93.0% | >98% |

TABLE 1-continued

| | Deuterated-methylating agent | Process | Yield | UPLC Purity |
|---|---|---|---|---|
| Reference example 5 | methyl-d$_3$ 4-methylbenzenesulfonate | 2 | 95.8% | >99.8% |

The UPLC purity was measured with Waters Acquity Ultra Performance LC.

Process 1

(9S,13S,14S)-3-Hydroxy-17-benzylmorphinan hydrobromide (24 mmol) was suspended in DMF (60 mL), and NaO$^t$Bu (51 mmol) and deuterated-methylating agent (26 mmol) were added to the obtained suspension at 10° C. or lower temperature. The mixture was stirred for 3 hours. After the reaction was terminated, toluene and water were added to the reaction mixture. The organic layer was separated and washed with water, and the solvent was removed. To the obtained residue were added NaHCO$_3$ (5 mmol), deuterated-methylating agent (29 mmol), and MeCN (40 mL), and the mixture was heated to reflux for 10 hours. Then, NaHCO$_3$ (5 mmol) and water (20 mL) were added to the reaction mixture, and the mixture was further stirred at 80° C. for one hour. After cooling the reaction mixture, 5% Pd/C (0.5 g) was added to the reaction mixture, and the reaction mixture was stirred under hydrogen atmosphere at room temperature for 16 hours. The reaction mixture was filtrated through Celite and washed with MeOH and water, and most of the organic solvent was removed from the filtrate. To the concentrated residue were added toluene, water, and 25% aqueous NaOH. The organic layer was separated, the organic layer was washed with water, and the solvent was removed to give the desired product.

Process 2

(9S,13S,14S)-3-Hydroxy-17-benzylmorphinan (24 mmol), deuterated-methylating agent (50 mmol), and NaHCO$_3$ (6 mmol) were suspended in MeCN (25 mL), and the suspension was heated to reflux for 4 hours. After the reaction was terminated, the reaction solution was cooled to 0° C., and 48% aqueous NaOH (3.0 g) was added thereto. The mixture was stirred at 0° C. for 16 hours and further at 80° C. for 4 hours, and then cooled to room temperature. To the mixture was added 10% Pd/C (0.6 g), and the mixture was stirred under hydrogen atmosphere at room temperature for 19 hours. The reaction mixture was filtrated through Celite and washed with MeCN and purified water, and most of the organic solvent was removed from the filtrate. To the concentrated residue were added MeCN, purified water, and 25% aqueous NaOH (5.5 mL). The organic layer was separated, the organic layer was washed with water, and the solvent was removed to give the desired product.

Example 1

Preparation of N-methyl-d$_3$ piperazine p-anisaldehyde
NaBH(OAc)$_3$

1) CD$_3$OTs, NaHCO$_3$
2) NH$_4$Cl

-continued

1) Pd(OH)$_2$/C, H$_2$
2) 48% NaOH

Benzyl piperazine-1-carboxylate (14.18 g) and 4-anisaldehyde (8.85 g) were dissolved in THF (200 mL), and the solution was cooled to 10° C. or lower temperature. To the solution was added sodium triacetoxyborohydride (16.37 g), and the mixture was stirred at 5 to 25° C. for 2 hours. Purified water (20 ml) was added to the reaction mixture, most of the solvent was removed in vacuo. To the residue was added 5N aqueous NaOH (20 ml), and the mixture was extracted with MTBE. The solvent was removed from the extract. To the residue were added methyl-d$_3$ 4-methylbenzenesulfonate (13.32 g, purity: 92%) and NaHCO$_3$ (0.54 g), and the mixture was suspended in MeCN. The suspension was heated to reflux for 4 hours. And, then stirred at room temperature for 16 hours. And, NH$_4$Cl (0.34 g) was added to the reaction mixture, and the mixture was heated to reflux for one hour and then cooled to room temperature. To the obtained suspension was added methanol (50 mL), and the reaction was purged with nitrogen. 10% Pd(OH)$_2$/C (0.5 g) was added to the reaction mixture, and the reaction mixture was stirred under hydrogen atmosphere at one atm pressure at 50° C. for 8 hours and then at room temperature for 16 hours. The reaction mixture was filtrated, and the solvent was removed from the filtrate. The residue was dissolved in THF (50 mL), the solution was cooled to 0° C., and then 48% aqueous NaOH (4.3 ml) was added dropwise thereto. The obtained suspension was filtrated, and washed with MTBE and a small amount of THF. And, most of the solvent was removed under reduced pressure from the filtrate. The residue was distilled under reduced pressure to obtain the desired product as a mixture with 4-methylanisole (3.89 g, yield 77.4%).

$^1$H-NMR (CDCl$_3$) δ; 2.88-2.91 (8H, m)

Example 2

Preparation of N-methyl-d$_3$-azepan-4-one

TsOH•H$_2$O
HOCH$_2$CH$_2$OH

1) CD$_3$OTs, NaI, NaHCO$_3$
2) Et$_3$N

-continued

Pd/C, H$_2$ c•HCl

1) Preparation of 8-benzyl-1,4-dioxa-8-azaspiro[4,6] undecene

To 1-benzylazepan-4-one (2.5 g) and para-toluenesulfonic acid hydrate (2.34 g) was added toluene (25 mL), and the mixture was heated to reflux for one hour. The reaction mixture was cooled to 60° C., and ethylene glycol (0.75 mL) was added thereto, and the reaction mixture was heated to reflux for additional 2 hours. The reaction mixture was cooled to room temperature, then 25% aqueous NaOH was added thereto, and the organic layer was separated. The obtained organic layer was concentrated, and the obtained residue was purified by column chromatography (AcOEt/ hexane) to give the desired product (535 mg).

2) Preparation of 8-methyl-d$_3$-1,4-dioxa-8-azaspiro [4,6]undecene

To 8-benzyl-1,4-dioxa-8-azaspiro[4,6]undecene (0.53 g) were added methyl-d$_3$ 4-methylbenzenesulfonate (0.51 g, purity: 87%), NaI (32 mg), and NaHCO$_3$ (18 mg). The mixture was suspended in MeCN (3 mL), and the suspension was stirred at 95° C. for 4 hours in a sealed reactor. The reaction mixture was cooled to room temperature, and TEA (0.15 mL) was added thereto, and the reaction mixture was stirred at 50° C. for 2 hours. To the obtained solution was added 10% Pd/C (50 mg), and the mixture was stirred under hydrogen atmosphere at one atm pressure at room temperature for 16 hours. The reaction mixture was filtered through Celite, and the filtrate was extracted with DCM to give the desired product (342 mg).

$^1$H-NMR (CDCl$_3$) δ; 1.65-1.75 (2H, m), 1.89 (2H, t, J=5.6 Hz), 1.97 (2H, t, J=5.6 Hz), 2.53 (2H, t, J=5.6 Hz), 2.59 (2H, t, J=5.6 Hz), 3.89 (4H, s).

3) Preparation of N-methyl-d$_3$-azepan-4-one

8-Methyl-d$_3$-1,4-dioxa-8-azaspiro[4,6]undecene (340 mg) was dissolved in THF (2.0 mL), concentrated hydrochloric acid (0.5 mL) was added thereto, and the obtained mixture was stirred at 60° C. for 3 hours. The reaction solution was cooled to room temperature, and the solvent, was removed to give the desired hydrochloride quantitatively. The obtained product was used in the next step without purification.

Example 3

Preparation of 1-(methyl-d$_3$)-1,4-diazepane

1) Preparation of benzyl 4-benzyl-1,4-diazepane-1-carboxylate

N-benzyl homopiperazine (4.18 mL) and DCM (21.5 mL) were mixed, and benzyl chloroformate (CbzCl) (3.55 mL) was added dropwise the mixture. The reaction solution was stirred at room temperature overnight, and optionally CbzCl (0.65 mL) was further added thereto depending on the reaction progress. The solvent was removed, and AcOEt was added to the obtained residue. The solvent was removed to give the desired product.

$^1$H-NMR (CDCl$_3$) δ; 1.77-1.91 (2H, m), 2.56-2.72 (4H, m), 3.49-3.60 (4H, m), 3.61 (2H, d, J=3.3 Hz), 5.14 (2H, d, J=2.4 Hz), 7.25-7.43 (10H, m).

2) Preparation of benzyl 4-(methyl-d$_3$)-1,4-diazepane-1-carboxylate

Benzyl 4-benzyl-1,4-diazepane-1-carboxylate (6.6 g), methyl-d$_3$ 4-methylbenzenesulfonate (4.32 g), NaHCO$_3$ (0.34 g), NaI (0.31 g), and MeCN (20 mL) were mixed, and the mixture was stirred under reflux for 8 hours. To the reaction mixture were added water (13 mL) and NH$_4$Cl (0.33 g), and the mixture was heated to reflux for 1.5 hours. The solvent was removed, and MeCN (27 mL), water (3 mL), and 10% Pd/C (660 mg) were added to the obtained residue. The mixture was stirred under hydrogen atmosphere at pressure of 0.4 MPa at 40° C. for 8 hours. The reaction mixture was filtrated, and the solvent was removed from the filtrate. To the residue were added AcOEt and water. The solution was basified with 5N aqueous NaOH, and extracted with AcOEt. The solvent was removed to give the desired product (3.81 g).

$^1$H-NMR (CDCl$_3$) δ; 1.83-1.92 (2H, m), 2.52-2.63 (4H, m), 3.51-3.64 (4H, m), 5.14 (2H, s), 7.28-7.39 (5H, m).

3) Preparation of 1-(methyl-d$_3$)-1,4-diazepane

Benzyl 4-(methyl-d$_3$)-1,4-diazepane-1-carboxylate (3.81 g), 10% Pd/C (380 mg), AcOEt (20 mL), and MeOH (5 mL) were mixed, and the mixture was stirred under hydrogen atmosphere at pressure of 0.4 MPa at 50° C. for 8 hours. The reaction mixture was filtrated, and the solvent was removed from the filtrate to give the desired product (1.74 g).

$^1$H-NMR (CDCl$_3$) δ; 1.82 (2H, quint, J=6.0 Hz), 2.58-2.64 (4H, m), 2.77 (1H, br s), 2.91-3.00 (4H, m).

Examples 4-22

The synthesis intermediates shown in Table 2 below can prepared from each corresponding starting compound in similar manner to Examples 1-3.

TABLE 2

| Example | Starting Compound | Synthesis Intermediate |
|---|---|---|
| Example 4 | | |
| Example 5 | | |
| Example 6 | | |

TABLE 2-continued

| Example | Starting Compound | Synthesis Intermediate |
|---------|-------------------|------------------------|
| Example 7 | | |
| Example 8 | | |
| Example 9 | | |
| Example 10 | | |
| Example 11 | | |
| Example 12 | | |
| Example 13 | | |
| Example 14 | | |
| Example 15 | | |

TABLE 2-continued

| Example | Starting Compound | Synthesis Intermediate |
|---|---|---|
| Example 16 | | |
| Example 17 | | |
| Example 18 | | |
| Example 19 | | |
| Example 20 | | |
| Example 21 | | |
| Example 22 | | |

Example 23

Preparation of N-(4-methyl-3-(4-(pyridin-3-yl)py-
rimidin-2-ylamino)phenyl)-4-((4-methyl-d₃-piper-
azin-1-yl)methyl)benzamide (deuterated imatinib)

-continued

-continued 4-(Chloromethyl)-N-(4-methyl-3-((4-(pyridin-3-yl)py-rimidin-2-yl)amino)phenyl)benzamide (0.43 g) and N-methyl-d₃-piperazine (1.33 g, purity: 77%) were dissolved in MeCN (40 mL), and the solution was heated to reflux for 6 hours. The reaction solution was concentrated to a volume of about 15 mL, and then stirred at 0° C. The precipitated crystal was collected on a filter, and washed with MeCN to give the desired product (370 mg).

$^1$H-NMR (DMSO-d$_6$); 2.23 (3H, s), 2.20-2.50 (8H, m), 3.52 (2H, s), 7.21 (1H, d, J=8.0 Hz), 7.40-7.57 (5H, m), 7.91 (1H, d, J=8.0 Hz), 8.08 (1H, d, J=2.0 Hz), 8.48 (1H, dt, J=2.0, 8.0 Hz), 8.51 (1H, d, J=4.8 Hz), 8.69 (1H, dd, J=2.0, 4.8 Hz), 8.99 (1H, s), 9.28 (1H, d, J=2.0 Hz), 10.18 (1H, s).

Example 24

Preparation of N-(5-((4-(ethyl-d₅)piperazin-1-yl)methyl)pyridin-2-yl)-5-fluoro-4-(4-fluoro-1-isopropyl-2-methyl-1H-benzo[d]imidazol-6-yl)pyrimidine-2-amine (deuterated abemaciclib)

The desired product can be prepared from 6-((5-fluoro-4-(4-fluoro-2-isopropyl-2-methyl-1H-benzo[d]imidazol-6-yl)pyrimidin-2-yl)amino)nicotinaldehyde and N-ethyl-d₅-piperazine in a manner disclosed in Tetrahedron Letters, 56, 949 (2015).

Example 25

Preparation of 2-(4-(ethyl-d₅)piperazin-1-yl)-4-(4-fluorophenyl)-5,6,7,6,9,10-hexahydrocycloocta[b]pyridine (deuterated blonanserin)

The desired product can be prepared front 2-chloro-4-(4-fluorophenyl)-5,6,7,3,9,10-hexahydrocycloocta[b]pyridine and N-ethyl-d₅-piperazine in a manner disclosed in U.S. Pat. No. 5,021,421 B.

Example 26

Preparation or 2-(2-ethoxy-5-((4-(ethyl-d₅)piperazin-1-yl)sulfonyl)phenyl)-5-methyl-7-propylimidazo[5,1-f][1,2,4]triazin-4(3H)-one (deuterated vardenafil)

The desired product can be prepared from 4-ethoxy-3-(5-methyl-4-oxo-7-propyl-3,4-dihydroimidazo[5,1-f][1,2,4]tri-azin-2-yl)benzenesulfonyl chloride and N-ethyl-d₅-pipera-zine in a manner disclosed in WO 1959/024433.

Example 27

Preparation of 2-methyl-4-(4-(methyl-d₃-piperazin-1-yl)-10H-benzo[b]thieno[2,3-e][1,4]diazepine (deuterated olanzapine)

The desired product car be prepared from 2-methyl-10H-benzo[b]thieno[2,3-e][1,4]diazepine-4-amine and N-methyl-d₃)piperazine in a manner disclosed in U.S. Pat. No. 5,229,382 B.

Example 28

Preparation of (S)-9-fluoro-3-methyl-10-(4-(methyl-d₃)piperazin-1-yl)-7-oxo-2,3-dihydro-7H-[1,4]oxazino[2,3,4-ij]quinoline-6-carboxylic acid (deuterated levofloxacin)

The desired product can be prepared from (S)-9,10-difluoro-3-methyl-7-oxo-2,3-dihydro-7H-[1,4]oxazino[2,3,4-ij]quinoline-6-carboxylic acid and N-methyl-d₃-piperazine in a manner disclosed in Journal of Medicinal Chemistry, 30, 2263 (1987).

Example 29

Preparation of 4-((2,4-dichloro-5-methoxyphenyl)amino)-6-methoxy-7-(3-(4-(methyl-d₃)piperazine-1-yl)propoxy)quinoline-3-carbonitrile (deuterated bosutinib)

The desired product can be prepared from 7-(3-chloropropoxy)-4-((2,4-dichloro-5-methoxyphenyl)amino)-6-methoxyquinoline-3-carbonitrile and N-methyl-d₃-piperazine in a manner disclosed in Journal of Medicinal Chemistry, 44, 3965 (2001).

Example 30

Preparation of (2-((5-chloro-2-((2-methoxy-4-(4-(4-(methyl-d₃)piperazin-1-yl)piperidin-1-yl)phenyl)amino)pyrimidin-4-yl) amino)phenyl)dimethylphosphine oxide (deuterated brigatinib)

1) Preparation of 1-(methyl-d₃)-4-(piperidin-4-yl) piperazine

The desired product can be prepared from 1-benzylpiperidin-4-one and N-methyl-d₃-piperazine in a manner disclosed in JP 2008-050307 A.

2) Preparation of Deuterated Brigatinib

The desired product can be prepared from 1-(methyl-d₃)-4-(piperidin-4-yl)piperazine in a manner disclosed in Journal of Medicinal Chemistry, 59, 4948 (2016).

Example 31

Preparation of 2-(3,5-bis(trifluoromethyl)phenyl)-N, 2-dimethyl-N-(6-(4-(methyl-d₃)piperazin-1-yl)-4-(o-tolyl)pyridin-3-yl)propanamide (deuterated brigatinib)

-continued

The desired product can be prepared from 2-(3,5-bis (trifluoromethyl)phenyl)-N-(6-chloro-(4-(o-tolyl)pyridin-3-yl)-N,2-dimethyl propanamide and N-methyl-d₃-piperazine in a manner disclosed in CK 107699500 A.

Example 32

Preparation of methyl (Z)-3-(((4-(N-methyl-2-(4-(methyl-d₃)piperazine-1-yl)acetamide)phenyl) amino)(phenyl)methylene)-2-oxoindoline-6-carboxylate (deuterated nintedanib)

The desired product can be prepared from methyl (Z)-3-(((4-(2-chloro-N-methylacetamide)phenyl)amino)(phenyl) methylene)-2-oxoindoline-6-carboxylate and N-methyl-d$_3$-piperazine in a manner disclosed in Synthetic Communications, 47, 975 (2017).

Example 33

Preparation of 6-ethyl-3-((3-methoxy-4-(4-(4-(methyl-d$_3$)piperazin-1-yl) piperidin-1-yl)phenyl) amino)-5-((tetrahydro-2H-pyran-4-yl)amino)pyra-zine-2-carboxamide (deliberated gilteritinib)

1) Preparation of 1-(methyl-d$_3$)-4-(piperidin-4-yl) piperazine hydrochloride

The desired product, can be prepared from tert-butyl 4-oxopiperidine-1-carboxylate and N-methyl-d$_3$-piperazine in a manner disclosed in WO2015/177326.

2) Preparation of Deuterated Gilteritinib

The desired product can be prepared from 1-(methyl-d$_3$)-4-(piperidin-4-yl)piperazine hydrochloride in a manner disclosed in WO2010/128659.

Example 34

Preparation of A-(4-chlorobenzyl)-2-(1-methyl-d$_3$-azepan-4-yl)phthalazin-1(2H)-one (deuterated azelastine)

4-(4-Chlorobenzyl)-2-(1-benzyl-azepan-4-yl)phthalazin-1(2H)-one (0.5 g), methyl-d$_3$ 4-methylbenzenesulfonate (0.25 g, purity: 92%), NaI (16 mg), and NaHCO$_3$ (18 mg) were suspended in MeCN (4 ml), and the suspension was stirred at 95° C. for 4 hours in a sealed reactor. In addition, the reaction suspension was stirred under open air condition at 50° C. for 30 minutes. Then, NH$_4$Cl (18 mg) and purified water (1 mL) were added thereto, and the mixture was stirred at 70° C. for additional one hour. To the obtained solution was added 10% Pd/C (25 mg), and the mixture was stirred under hydrogen atmosphere at one atm pressure at room temperature for 1.5 hours. The reaction mixture was filtered through Celite. To the filtrate was added aqueous ammonia, and the mixture was extracted with AcOEt. The solvent was removed from the extract, and the obtained residue was purified by column chromatography (AcOEt/ hexane) to give the desired product (368 mg).

$^1$H-NMR (CDCl$_3$) δ; 1.65-1.80 (1H, m), 1.90-2.15 (4H, m), 2.15-2.30 (1H, m), 2.50-2.30 (4H, m), 4.26 (2H, s), 5.30-5.40 (1H, m), 7.18-7.21 (2H, m), 7.25-7.27 (2H, m), 7.67-7.71 (3H, m), 8.44-8.47 (1H, m).

25

Example 35

Preparation of 1-(2-ethoxyethyl)-2-(4-methyl-d₃-1,
4-diazepan-1-yl)-1H-benzo[d]imidazole (deuterated
emedastine)

2-Chloro-(2-ethoxyethyl)benzimidazole (106 mg), 1-(methyl-d₃)-1,4-diazepane (83 mg), triethylamine (0.5 mL), and MeCN (0.5 mL) were mixed, and the mixture was heated to reflux for 8 days. To the reaction mixture were added AcOEt and water, and the mixture was extracted with AcOEt. The solvent was removed from the extract, and the obtained residue was purified by column chromatography (AcOEt/MeOH) to give the desired product (84 mg).

¹H-NMR (CDCl₃) δ; 1.15 (3H, t, J=7.0 Hz), 2.02 (2H, quint, J=5.8 Hz), 2.70-2.80 (4H, m), 3.46 (2H, q, J=7.0 Hz), 3.62-3.71 (4H, m), 3.78 (2H, t, J=6.1 Hz), 4.18 (2H, t, J=6.1 Hz), 7.07-7.18 (2H, m), 7.22-7.27 (1H, m), 7.51-7.56 (1H, m).

Example 36

Preparation of 2-(4-(methyl-d₃)-1,4-diazepan-1-yl)-
N-((5-methylpyrazin-2-yl)methyl)-5-oxo-5H-benzo
[4,5]thiazolo[3,2-a][1,8]naphthyridine-6-carboxam-
ide (deuterated CX-5461)

26

-continued

1) Preparation of methyl 2-(4-(methyl-d₃)-1,4-diaz-
epan-1-yl)-5-oxo-5H-benzo[4,5]thiazolo[3,2-a][1,8]
naphthyridine-6-carboxylate The desired product, can be prepared from methyl 2-chloro-5-oxo-5H-benzo[4,5]thiazolo[3,2-a][1,8]naphthy-ridine-6-carboxylate and 1-(methyl-d₃)-1,4-diazepane in a manner disclosed in ACS Medicinal Chemistry Letters, 3, 602 (2012).

2) Preparation of Deuterated CX-5461

The desired product can be prepared from methyl 2-(4-(methyl-d₃)-1,4-diazepan-1-yl)-5-oxo-5H-benzo[4,5]thi-azolo[3,2-a][1,8]naphthyridine-6-carboxylate in a manner disclosed in ACS Medicinal Chemistry Letters, 3, 602 (2012).

Example 37

Preparation of N-[2-(1-methyl-d$_3$-pyrrolidin-2-yl)
ethyl]-3-[(4,7-dihydro-7-oxo-1-methyl-3-propyl-1H-
pyrazolo[4,3-d]pyrimidin)-5-yl]-4-propoxybenzene-
sulfonamide (deuterated udenafil)

3-((5-Carbamoyl-1-methyl-3-propyl-1H-pyrazol-4-yl)
carbamoyl)-4-propoxybenzenesulfonylchloride and 2-(1-
(methyl-d$_3$)pyrrolidin-2-yl)ethane-1-amine are mixed, and
the mixture is stirred in DCM at room temperature. After the
reaction is terminated, aqueous NaHCO$_3$ is added thereto,
the mixture is extracted with AcOEt, and the solvent is
removed from the extract. To the obtained residue is added
tert-butanol, and the mixture is heated to reflux with potas-
sium tert-butoxide. To the reaction solution is added water,
and the mixture is extracted with AcOEt. The solvent is
removed from the extract to give the desired product.

Example 38

Preparation of N-((1-ethyl-d$_5$-2-pyrrolidinyl)
methyl)-2-methoxy-4-amino-5-(ethylsulfonyl)benz-
amide (deuterated amisulpride)

-continued 5-(Ethylsulfonyl)-2-methoxy-4-nitrobenzoic acid and (1-
(ethyl-d$_5$)pyrrolidin-2-yl)methaneamine are mixed in
dioxane in the presence of TEA and ethyl chloroformate, and
the mixture is stirred at room temperature. After the reaction
is terminated, water is added thereto, the mixture is extracted
with AcOEt, and the solvent is removed from the extract. To
the obtained residue are added EtOH and Raney nickel, and
the mixture is stirred under hydrogen atmosphere. The
reaction solution is filtrated to remove insoluble matters, and
the solvent is removed from the filtrate to give the desired
product.

Example 39

Preparation of (1R,3r,5S)-8-methyl-d$_3$-8-azabicyclo
[3.2.1]octan-3-yl 3-hydroxy-2-phenylpropanoate
(deuterated atropine)

3-Chloro-1-oxo-2-phenylpropylacetate and (1R,3r,5S)-8-
(methyl-d$_3$)-8-azacyclo[3,2,1]octan-3-ol are mixed, and the
mixture is stirred with methanesulfonic acid in DCM at
room temperature. After the reaction is terminated, aqueous
NaHCO$_3$ is added thereto, the mixture is extracted with
AcOEt, and the solvent is removed from the extract. To the
obtained residue is added MeOH, and the solution is stirred
with sodium methoxide at room temperature. To the reaction
solution is added water, and the mixture is extracted with
AcOEt. The solvent is removed from the extract to give the
desired product.

Example 40

Preparation of (1α,5α)-8-methyl-d₃-8-azabicyclo[3.2.1]octan-3β-yl 1H-indole-3-carboxylate (deuterated tropisetron)

1H-Indole-3-carboxylic acid and (1R,3r,5S)-8-(methyl-d₃-8-azabicyclo[3,2,1]octan-3-ol are mixed, and the mixture is heated to reflux in chloroform in the presence of p-toluenesulfonic acid. After the reaction is terminated, aqueous NaHCO₃ is added thereto, the mixture is extracted with AcOEt, and the solvent is removed from the extract.

Example 41

Preparation of (R)-3-((1-methyl-d₃-pyrrolidin-2-yl)methyl)-5-(2-(phenylsulfonyl)ethyl)-1H-indole (deuterated eletriptan)

1) Preparation of (S,E)-3-((1-benzylpyrrolidin-2-yl)methyl)-5-(2-(phenylsulfonyl)vinyl)-1H-indole A solution of benzyl d-prolinoyl chloride, ethylmagnesium bromide, zinc chloride, and 5-bromoindole in Et₂O is stirred at room temperature. After the reaction is terminated, water is added thereto, the mixture is extracted with AcOEt, and the solvent is removed from the extract. To the obtained residue are added aluminium hydride and THF, and the mixture is stirred at room temperature to 60° C. Subsequently, MeOH is added thereto, the solution is filtrated to remove insoluble matters, and the filtrate is concentrated. To the obtained residue are added MeCN followed by phenylvinylsulfone, palladium acetate, tri(o-tolyl)phosphine, and triethylamine, and the mixture is heated to reflux. To the reaction mixture is added water, and the mixture is extracted with AcOEt. The solvent, is removed from the extract to give the desired product.

2) Preparation of Deuterated Eletriptan

The desired product can be prepared from (S,E)-3-((1-benzylpyrrolidin-2-yl)methyl)-5-(2-(phenylsulfonyl)vinyl)-1H-indole and methyl-d₃ 4-methylbenzenesulfonate in a manner disclosed in Reference examples 1-5.

Example 42

Preparation of (S)-3-(1-methyl-d₃-pyrrolidin-2-yl)pyridine (deuterated nicotine)

1) Preparation of Dibenzyl Nornicotinium

A mixture of nornicotine, Na$_2$CO$_3$, and benzyl bromide is stirred in MeOH at room temperature. The solvent is removed from the reaction mixture to give dibenzyl nornicotinium.

2) Preparation of Deuterated Nicotine

The desired product can be prepared from dibenzyl nornicotinium in a manner disclosed in Reference examples 1-5.

Example 43

Preparation of (3aR,8aS)-3a,8-dimethyl-1-(methyl-d$_3$)-1,2,3,3a,8,8a-hexahydropyrrolo[2,3-b]indol-5-yl phenylcarbamate (deuterated phenserine)

1) Preparation of (3aR,8aS)-5-methoxy-3a,8-dimethyl-1-(methyl-d$_3$)-1,2,3,3a,8,8a-hexahydropyrrolo[2,3-b]indole (3aR,8aS)-1-Benzyl-5-methoxy-3a,8-dimethyl-1,2,3,3a,8,8a-hexahydropyrrolo[2,3-b]indole (5.0 g), methyl-d$_3$ 4-methylbenzenesulfonate (3.37 g), NaHCO$_3$ (272 mg), NaI (243 mg), and MeCN (20 mL) were mixed, and the mixture was stirred at 90° C. for 7 hours in a sealed reactor. NH$_4$Cl (260 mg) and water (10 mL) were added thereto, and the mixture was stirred at 70° C. for one hour in the sealed reactor. 10% Pd/C (500 mg) was added thereto, and the reaction mixture was stirred under hydrogen atmosphere at pressure of 0.4 MPa at 40° C. for 6 hours. The reaction mixture was filtrated through Celite. To the filtrate were added AcOEt and water, and the solution was basified with 5N aqueous NaOH and extracted with AcOEt. The solvent was removed from the extract, and the obtained residue was purified by column chromatography (AcOEt/hexane) to give the desired product (1.67 g).

$^1$H-NMR (CDCl$_3$) δ; 1.43 (3H, s), 1.91-1.97 (2H, m), 2.59-2.74 (2H, m), 2.89 (3H, s), 3.75 (3H, s), 4.05 (1H, s), 6.36 (1H, d, J=8.4 Hz), 6.61-6.68 (2H, m).

2) Preparation of (3aR,8aS)-3a,8-dimethyl-1-(methyl-d$_3$)-1,2,3,3a,8,8a-hexahydropyrrolo[2,3-b]indol-5-ol (3aR,8aS)-5-Methoxy-3a,8-dimethyl-1-(methyl-d$_3$)-1,2,3,3a,8,8a-hexahydropyrrolo[2,3-b]indole (367 mg) and DCM (6 mL) were mixed, and the mixture was cooled in an ice bath. BBr$_3$ (1.59 mL, 17% DCM solution) was slowly added dropwise to the cooled solution. The reaction solution was stirred at room temperature for 6 hours, and optionally BBr$_3$ (0.48 mL, 17% DCM solution) was further added thereto depending on the reaction progress. The solvent was removed from the reaction solution. To the obtained residue were added water and saturated aqueous sodium bicarbonate, and the mixture was extracted with AcOEt. The solvent was removed from the extract, and the obtained residue was purified by column chromatography (AcOEt/MeOH) to give the desired product (163 mg).

$^1$H-NMR (DMSO-d$_6$) δ; 1.32 (3H, s), 1.68-1.86 (2H, m), 2.37-2.46 (1H, m), 2.58-2.66 (1H, m), 2.75 (3H, s), 3.95 (1H, s), 6.26 (1H, d, J=8.1 Hz), 6.40-6.46 (2H, m), 8.54 (1H, s).

3) Preparation of Deuterated Phenserine (3aR,8aS)-3a,8-Dimethyl-1-(methyl-d$_3$)-1,2,3,3a,8,8a-hexahydropyrrolo[2,3-b]indol-5-ol (143 mg) and THF (13 mL) were mixed, and the mixture was stirred with sodium hydride (2.8 mg) at room temperature for 10 minutes. Phenyl isocyanate (85 μL) was added thereto, and the mixture was stirred at room temperature for 5 hours. The solvent was removed from the reaction solution. To the obtained residue were added water and saturated aqueous sodium bicarbonate, and the mixture was extracted with AcOEt. The solvent was removed from the extract, and the obtained residue was purified by column chromatography (AcOEt/hexane) to give the desired product (146 mg).

$^1$H-NMR (DMSO-d$_6$) δ; 1.36 (3H, s), 1.78-1.87 (2H, m), 2.44-2.53 (1H, m), 2.61-2.67 (1H, m), 2.86 (3H, s), 4.10 (1H, s), 6.39 (1H, d, J=8.4 Hz), 6.80 (1H, dd, J=8.4, 2.4 Hz), 6.85 (1H, d, J=2.4 Hz), 6.99-7.05 (1H, m), 7.27-7.33 (2H, m), 7.50 (2H, d, J=7.7 Hz), 10.05 (1H, s).

Example 44

Preparation of 2-methyl-d₃-1,2,3,4,10,14b-hexahydrobenzo[c]pyrazino[1,2-a]pyrido[3,2-f]azepine (deuterated mirtazapine)

¹H-NMR (CDCl₃) δ; 2.36 (1H, dt, J=3.2, 10.8 Hz), 2.52 (1H, t, J=10.8 Hz), 2.90-3.00 (2H, m), 3.43 (1H, d, J=13.2 Hz), 3.48 (1H, dt, J=2.8, 12.4 Hz), 3.72 (1H, dt, J=2.8, 13.2 Hz), 3.86 (2H, s), 4.36 (1H, d, J=8.0 Hz), 4.52 (1H, d, J=13.2 Hz), 6.73 (1H, dd, J=4.8, 7.2 Hz), 7.10-7.20 (4H, m), 7.30-7.40 (6H, m), 8.16 (1H, d, J=3.2 Hz).

2) Preparation of Deuterated Mirtazapine

2-Benzyl-1,2,3,4,10,14b-hexahydrobenzo[c]pyrazino[1, 2-a]pyrido[3,2-f]azepine (435 mg), methyl-d₃ 4-methylbenzenesulfonate (297 mg), and NaHCO₃ (16 mg) were suspended in MeCN (5 mL), and the suspension was heated to reflux for 4 hours. After the reaction was completed, the reaction solution was cooled to 0° C., and aqueous NH₄Cl (31 mg/0.8 mL) was added thereto. The reaction mixture was stirred at 60° C. for 3 hours, and then cooled to room temperature. To the obtained solution was added 10% Pd/C (50 mg), and the mixture was stirred under hydrogen atmosphere at room temperature for 18 hours. The reaction mixture was filtered through Celite, and most of the organic solvent in the filtrate was removed. The obtained residue was purified by column chromatography (AcOEt/hexane) to give the desired product (110 mg).

¹H-NMR (CDCl₃) δ; 2.50 (1H, td, J=10.8, 3.2 Hz), 2.63 (1H, t, J=10.8 Hz), 3.02 (1H, d, J=11.2 Hz), 3.14 (1H, d, J=11.2 Hz), 3.42 (1H, d, J=13.2 Hz), 3.55 (1H, td, J=2.8, 12.4 Hz), 3.77 (1H, dt, J=2.8, 13.2 Hz), 4.47 (1H, dd, J=2.4, 10.4 Hz), 4.50 (1H, d, J=13.2 Hz), 6.79 (1H, dd, J=5.2, 7.6 Hz), 7.15 (4H, m), 7.33 (1H, d, J=8.4 Hz), 8.16 (1H, dd, J=2.0, 9.2 Hz).

Example 45

Preparation of 5-((3,4-dimethoxyphenethyl)(methyl-d₃)amino)-2-(3,4-dimethoxyphenyl)-2-isopropylpentanenitrile (deliberated verapamil) hydrochloride

1) Preparation of 2-benzyl-1,2,3,4,10,14b-hexahydrobenzo[c]pyrazino[1,2-a]pyrido[3,2-f]azepine 1,2,3,4,10,14b-Hexahydrobenzo[c]pyrazino[1,2-a]pyrido [3,2-f]azepine (607 mg), K₂CO₃ (434 mg), and benzyl bromide (475 mg) were stirred in DMF at room temperature for 3 hours. To the reaction solution was added water, and the mixture was extracted with AcOEt. The solvent was removed from the extract to give the desired product (570 mg).

5-(Benzyl(3,4-dimethoxyphenethyl)amino)-2-(3,4-dimethoxyphenyl)-2-isopropylpentane-nitrile (100 mg), methyl-d₃ 4-methylbenzenesulfonate (43 mg, purity: 92%), NaI (2.8 mg), and NaHCO₃ (1.6 mg) were suspended in MeCN (0.5 mL), and the suspension was stirred in a sealed reactor at 95° C. for 5 hours and then at room temperature overnight. NH₄Cl (3.0 mg) and purified water (0.2 mL) were added thereto, and the mixture was stirred at 60° C. for additional 3 hours. To the obtained solution was added 20% Pd(OH)₂/C (5 mg), and the mixture was stirred under hydrogen atmosphere at one atm pressure at room temperature for 16 hours. The reaction mixture was filtered through Celite, and aqueous NaOH was added to the filtrate. The mixture was extracted with AcOEt, and the solvent was removed from the extract. The obtained residue was dissolved in toluene, and a solution of hydrogen chloride in $Et_2O$ (0.19 mL) was added thereto. The mixture was stirred at room temperature for one hour, and the precipitated crystal was collected on a filter to give the desired product (60 mg).

$^1$H-NMR (CDCl$_3$) δ: 0.79 (3H, d, J=6.4 Hz), 1.10-1.18 (1H, m), 1.18 (3H, d, J=6.4 Hz), 1.49-1.65 (1H, m), 1.78-1.88 (1H, m), 2.00-2.15 (2H, m), 2.28-2.41 (2H, m), 2.45-2.55 (2H, m), 2.60-2.70 (2H, m), 3.85 (3H, s), 3.87 (3H, s), 3.88 (3H, s), 3.88 (3H, s), 6.67-6.71 (2H, m), 6.77-6.86 (3H, m), 6.88-6.93 (1H, m).

Examples 46 and 47

The desired products shown in Table 3 below can be prepared from each corresponding starting compound in similar manner to Examples 23 and 26.

Example 48

Preparation of N-ethyl-d$_5$ piperazine

1) C$_2$D$_5$OTs, NaHCO$_3$, NaI
2) NH$_4$Cl

TABLE 3

| Example | Starting Compound | Deuterated alkylating agent |
|---|---|---|
| Example 46 | | |
| Example 47 | | |

| Example | Desired Product |
|---|---|
| Example 46 | |
| Example 47 | |

-continued

1) Preparation of benzyl
4-(ethyl-d₅)piperazine-1-carboxylate

Benzyl 4-(4-methoxybenzyl)piperazine-1-carboxylate (10 g), ethyl-d₅ 4-methylbenzenesulfonate (6.84 g), NaHCO₃ (0.49 g), sodium iodide (0.44 g), and MeCN (40 mL) were mixed, and the mixture was stirred at 90° C. for 2 days in a sealed reactor. Water (20 mL) and NH₄Cl (0.47 g) were added thereto, and the mixture was stirred at 90° C. for one hour in the sealed reactor. 10% Pd/C (1 g) was added to the reaction solution, and the mixture was stirred under hydrogen atmosphere at pressure of 0.4 MPa at 40° C. for 4 hours. The reaction solution was filtrated through Celite, and the filtrate was concentrated. To the obtained residue were AcOEt and water, and the solution was basified with 5N aqueous NaOH and extracted with AcOEt. The solvent was removed from the extract to give the desired product (5.06 g).

$^1$H-NMR (CDCl₃) δ; 2.40 (4H, br s), 3.53 (4H, t, J=5.1 Hz), 5.13 (2H, s), 7.30-7.38 (5H, m).

2) Preparation of N-ethyl-d₅ piperazine

Benzyl 4-(ethyl-d₅)piperazine-1-carboxylate (5.06 g), 10% Pd/C (500 mg), AcOEt (26 mL), and MeOH (6.5 mL) were mixed, and stirred under hydrogen atmosphere at pressure of 0.4 MPa at 50° C. for 12 hours. The reaction mixture was filtered through Celite, and the filtrate was concentrated to give the desired product as a mixture with 4-methylanisole (2.09 g, yield 74.5%).

$^1$H-NMR (CDCl₃) δ; 2.84-2.93 (8H, m).

INDUSTRIAL APPLICABILITY

The present invention makes it possible to mono-deuterated-lower-alkylate an amine moiety in high yield and low cost.

The invention claimed is:

1. A method of introducing a mono-deuterated lower-alkyl into a secondary amine in a compound having a secondary amine, comprising replacing a hydrogen atom in the secondary amine by an aralkyl to obtain a tertiary amine, lower-alkylating the obtained tertiary amine with a deuterated-lower-alkylating agent under neutral or basic condition, and then eliminating the aralkyl group, wherein the aralkyl is a benzyl derivative selected from the group consisting of benzyl, 4-nitrobenzyl, 4-methoxybenzyl, 2-nitrobenzyl, 4-chlorobenzyl, 2,6-dichlorobenzyl, 4-methylbenzyl, and 2,4,6-trimethylbenzyl, and the compound having the secondary amine is a linear secondary amine or a compound having a piperidine, piperazine, pyrrolidine, azepane, diazepane, morpholine, azocane, or azetidine structure, which is a single ring system or a part of a bicyclic, tricyclic, or tetracyclic system.

2. The method of claim 1, wherein the compound having the secondary amine is not the compound having the piperidine structure.

3. The method of claim 1, wherein the mono-deuterated lower-alkyl is deuterated methyl or deuterated ethyl, and the deuterated-lower-alkylating agent is deuterated-methylating agent or deuterated-ethylating agent.

4. The method of claim 1, wherein the mono-deuterated-lower-alkyl is deuterated methyl, and the deuterated-lower-alkylating agent is methyl-d₃ methanesulfonate, methyl-d₃ benzenesulfonate, methyl-d₃ 4-methylbenzenesulfonate, methyl-d₃ 2-nitrobenzenesulfonate, methyl-d₃ 4-nitrobenzenesulfonate, dimethyl-do sulfate, dimethyl-d₆ carbonate, methyl-d₃ trifluoromethanesulfonate, bromomethyl-d₃, or iodomethyl-d₃.

5. The method of claim 1, wherein the mono-deuterated lower-alkyl is deuterated ethyl, and the deuterated-lower-alkylating agent is ethyl-d₅ methanesulfonate, ethyl-d₅ benzenesulfonate, ethyl-d₅ 4-methylbenzenesulfonate, ethyl-d₅ 2-nitrobenzenesulfonate, ethyl-d₅ 4-nitrobenzenesulfonate, diethyl-d₁₀ sulfate, diethyl-d₁₀ carbonate, ethyl-d₅ trifluoromethanesulfonate, bromoethyl-d₅, or iodoethyl-d₅.

6. The method of claim 1, wherein the benzyl derivative is benzyl or 4-methoxybenzyl.

7. The method of claim 1, wherein the eliminating the aralkyl group is carried out by hydrogenation.

8. The method of claim 1, wherein the basic condition is adjusted with sodium carbonate, cesium carbonate, potassium carbonate, sodium bicarbonate, potassium bicarbonate, sodium hydride, potassium hydride, sodium hydroxide, potassium hydroxide, sodium tert-butoxide, potassium tert-butoxide, alkyllithium, lithium amide, sodium methoxide, or tert-amine.

9. The method of claim 1, wherein the basic condition is adjusted with lithium diisopropylamide, or lithium hexamethyldisilazide.

* * * * *